(12) United States Patent
Ishikawa

(10) Patent No.: US 10,852,474 B2
(45) Date of Patent: Dec. 1, 2020

(54) OPTICAL FIBER BUNDLE, ENDOSCOPE, AND METHOD OF PRODUCING OPTICAL FIBER BUNDLE

(71) Applicant: OLYMPUS CORPORATION, Tokyo (JP)

(72) Inventor: Yuki Ishikawa, Mitaka (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/697,303

(22) Filed: Nov. 27, 2019

(65) Prior Publication Data

US 2020/0103590 A1 Apr. 2, 2020

Related U.S. Application Data

(63) Continuation of application No. PCT/JP2018/019520, filed on May 21, 2018.

(30) Foreign Application Priority Data

May 31, 2017 (JP) ................................ 2017-108027

(51) Int. Cl.
*G02B 6/02* (2006.01)
*A61B 1/00* (2006.01)
(Continued)

(52) U.S. Cl.
CPC ...... *G02B 6/02395* (2013.01); *A61B 1/00167* (2013.01); *G02B 6/04* (2013.01); *G02B 6/3861* (2013.01); *G02B 23/26* (2013.01)

(58) Field of Classification Search
CPC .... G02B 6/02395; G02B 6/04; G02B 6/3861; G02B 23/26; A61B 1/00167
See application file for complete search history.

(56) References Cited

U.S. PATENT DOCUMENTS 5,694,513 A * 12/1997 Okaniwa ............ C08G 73/1039
385/123
2016/0231505 A1* 8/2016 Miyata .................. G02B 23/26

FOREIGN PATENT DOCUMENTS

JP H03-12607 A 1/1991
JP 2006-47426 A 2/2006
(Continued)

OTHER PUBLICATIONS

International Search Report dated Aug. 21, 2018 issued in PCT/JP2018/019520.
(Continued)

*Primary Examiner* — Chris H Chu
(74) *Attorney, Agent, or Firm* — Scully, Scott, Murphy & Presser, P.C.

(57) ABSTRACT

An object of the present invention is to provide an optical fiber bundle having high adhesive strength at an end, and an endoscope using the optical fiber bundle. Another object of the present invention is to provide a method of producing the optical fiber bundle having high adhesive strength at an end. An embodiment of the present invention provides an optical fiber bundle including a bundle of optical transmission elements, each of which includes a fiber including a core made of a first glass and a cladding made of a second glass and covering an outer periphery of the core, and a covering layer covering the outer periphery of the cladding. The covering layer includes an alkyl group having 1 to 7 carbon atoms and not being fluorine-substituted. The alkyl group is bonded to the cladding via a siloxane bond.

15 Claims, 4 Drawing Sheets

(51) Int. Cl.
*G02B 6/04* (2006.01)
*G02B 6/38* (2006.01)
*G02B 23/26* (2006.01)

(56) References Cited

FOREIGN PATENT DOCUMENTS

| | | |
|---|---|---|
| JP | 5855798 B2 | 2/2016 |
| JP | 2017-7875 A | 1/2017 |
| WO | WO 2015/087600 A1 | 6/2015 |

OTHER PUBLICATIONS

English translation of International Preliminary Report on Patentability dated Dec. 12, 2019, together with the Written Opinion received in related International Application No. PCT/JP2018/019520.

* cited by examiner

OPTICAL FIBER BUNDLE, ENDOSCOPE, AND METHOD OF PRODUCING OPTICAL FIBER BUNDLE

CROSS-REFERENCE TO RELATED APPLICATIONS

This application is a Continuation Application of PCT Application No. PCT/JP2018/019520, filed May 21, 2018 and based upon and claiming the benefit of priority from prior Japanese Patent Application No. 2017-108027, filed May 31, 2017, the entire contents of all of which are incorporated herein by reference.

BACKGROUND OF TEE INVENTION

1. Field of the Invention

The present invention relates to an optical fiber bundle, an endoscope, and a method of producing the optical fiber bundle.

2 Description of the Related Art

In a conventional endoscope, a glass optical fiber containing lead is used for the purpose of transmitting illumination light from a light source to a tip part of the endoscope in order to secure brightness during observation. The lead-containing optical fiber has excellent transmissivity/light distribution properties. However, because of strict regulations on detrimental substances such as lead, there is a risk that the lead-containing optical fiber will be unusable for endoscopes in the future. For this reason, various lead-free optical fibers have been developed. Lead-free optical fibers are however harder and less flexible in terms of physical properties than lead-containing optical fibers, and thus have a problem of being broken and deteriorating the observation performance of the endoscope when subjected to severe-angle bending at the tip part of the endoscope.

To solve the above problem, for example, Japanese Patent No. 5855798 discloses a technique for improving durability and abrasion resistance of an optical fiber (hereinafter also referred to as a "fiber") including a core and a cladding by covering the outer periphery of the optical fiber with a covering layer including a specific alkylsilane (hereinafter referred to as an "alkylsilane layer"). This technique makes it possible to reduce the breaking and deterioration of lead-free optical fibers to such an extent that sufficient observation performance of endoscopes is obtained.

BRIEF SUMMARY OF THE INVENTION

Japanese Patent No. 5855798 shows FIGS. 8 and 9 as an example of a light guide or an image guide. FIG. 9 is a cross-sectional view of the image guide or light guide taken along line IV-IV in FIG. 8. In this example, an optical fiber bundle constituted of a bundle of a large number of optical transmission elements 113 is accommodated in a jacket tube 111. Each end of the jacket tube is provided with a ferrule 112.

Some endoscopes are required to have a smaller diameter for use in a smaller space than typical endoscopes. The demand for such an endoscope with a smaller diameter increases demand for an optical fiber bundle with end faces formed in a predetermined shape without using a ferrule at the end.

Such an optical fiber bundle with its end face formed in a predetermined shape without using a ferrule is likely to be damaged at its end due to insufficient adhesion between the optical transmission elements. Stronger adhesion between the optical transmission elements is thus required as compared to the case of using a ferrule. However, intensive studies by the present inventors have found that if an optical fiber bundle with its end face formed without using a ferrule is produced by using optical transmission elements produced through the technique of covering with a specific alkylsilane layer described in Japanese Patent No. 5855798, the optical fiber bundle has sufficient durability but is likely to be damaged at its end due to insufficient adhesion between the optical transmission elements.

An aspect of the present invention provides an optical fiber bundle including a bundle of optical transmission elements, each of which includes a fiber including a core made of a first glass and a cladding made of a second glass and covering an outer periphery of the core, and a covering layer covering an outer periphery of the cladding, wherein the covering layer includes an alkyl group having 1 to 7 carbon atoms and not being fluorine-substituted, and wherein the alkyl group is bonded to the cladding via a siloxane bond.

Another aspect of the present invention provides a method of producing the optical fiber bundle, including: applying a treatment liquid including alkylsilane which includes an alkyl group having 1 to 7 carbon atoms and not being fluorine-substituted, to the outer periphery of the cladding to form the covering layer on the outer periphery of the cladding, thereby obtaining each optical transmission element;

bundling a plurality of the optical transmission elements to obtain a bundle of optical transmission elements;

preparing a jig including a through hole into which an end of the bundle is to be inserted;

inserting at least one end of the bundle into the through hole of the jig until a tip part of the end protrudes;

applying an adhesive to the end of the bundle including a protrusion that protrudes from the through hole to fix the end; and cutting the protrusion and polishing an end face.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Embodiments of the present invention will be described below.

A first embodiment of the present invention is an optical fiber bundle including a bundle of optical transmission elements. In one embodiment, the optical fiber bundle is fixed at least at one end with an adhesive. In another embodiment, the optical fiber is free from a ferrule covering an outer periphery of the end fixed with the adhesive.

Figure 1:
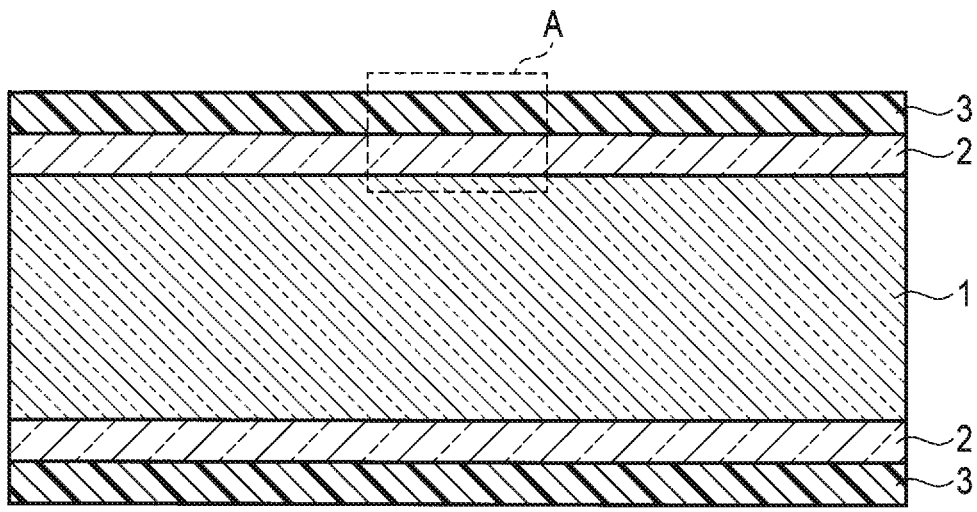
FIG. 1 is an axial cross-sectional view of an optical transmission element included in an optical fiber bundle according to an embodiment.

FIG. 1 is an axial cross-sectional view of an optical transmission element included in an optical fiber bundle according to an embodiment.

The optical transmission element means one used as a light waveguide for propagating a light wave, a signal, an image, or the like, and includes, for example, an optical fiber, a light guide, and an optical fiber sensor. The optical transmission element may have a circular or rectangular cross-section without particular limitation.

The optical transmission element according to the embodiment includes a fiber and a covering layer 3.

In the optical transmission element, the fiber mainly transmits light. The fiber includes a core 1 formed in a cylindrical shape and a cladding 2 covering the outer periphery of the core. The core 1 is made of a first glass, and the cladding 2 is made of a second glass. These glasses preferably have high optical transparency. The first glass constituting the core 1 has a higher refractive index than the second glass constituting the cladding 2. Examples of the first glass and the second glass include silica glass.

The covering layer 3 mainly protects the fiber and adjusts the adhesion between a plurality of optical transmission elements when the optical transmission elements are bundled. The covering layer 3 covers the outer periphery of the cladding 2. The thickness of the covering layer 3 is not particularly limited, but may be 1 nm to 100 nm, and is, for example, about 10 nm. When the covering layer 3 is too thin, the fiber cannot sufficiently be protected. On the other hand, when the covering layer is too thick, the ratio of the cross-sectional area of the fiber to the cross-sectional area of the optical transmission element is decreased, which may cause a decrease in the transmitting efficiency of light.

The covering layer 3 includes a plurality of alkyl groups, each of which has 1 to 7 carbon atoms and is not fluorine-substituted. Each alkyl group is bonded to the cladding via a siloxane bond.

In one embodiment, the alkyl group is preferably an alkyl group having 6 or 7 carbon atoms and not being fluorine-substituted.

In another embodiment, the alkyl group may be an alkyl group represented by $CH_3(CH_2)_m$—, where m represents an integer of 0 to 6, and is preferably 5 or 6, for example.

Figure 2A:
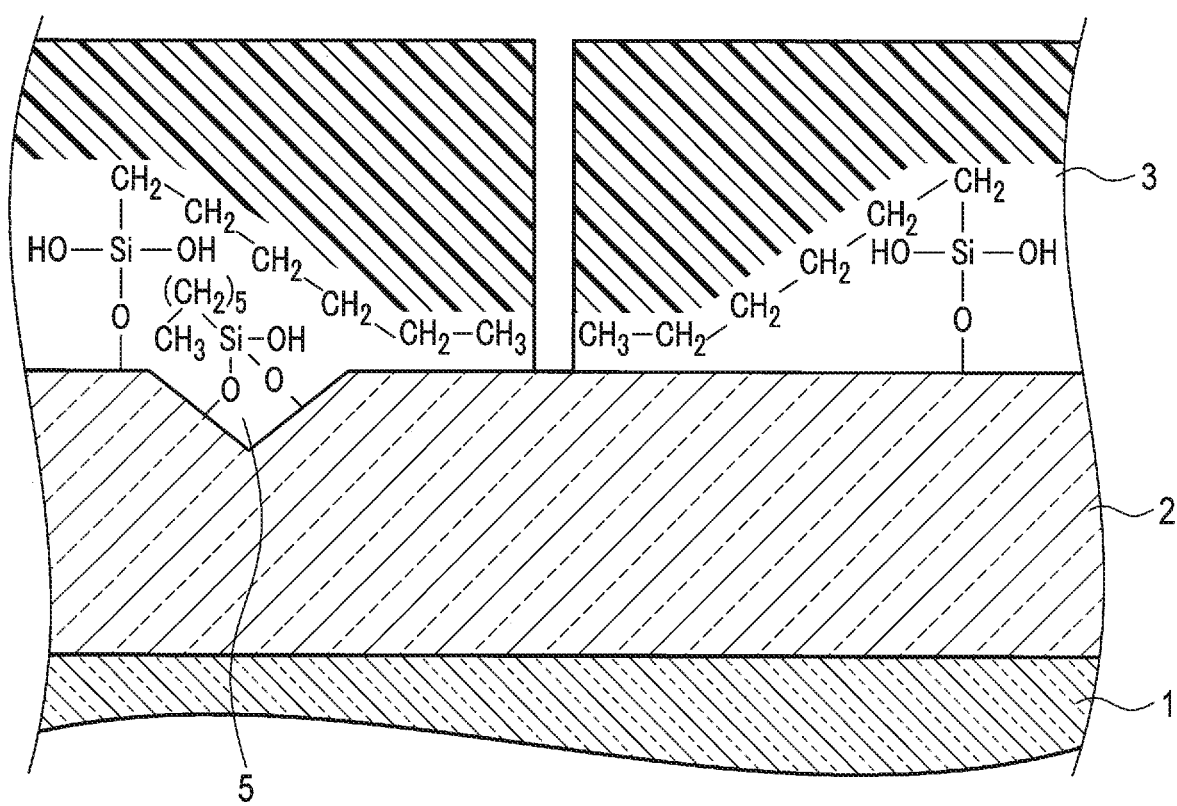
FIG. 2A is a magnified cross-sectional view of region A surrounded with a dashed line in FIG. 1, in which the number of carbon atoms of an alkyl group contained in a covering layer 3 is six.

FIG. 2A is an axial cross-sectional view of an optical transmission element included in an optical fiber bundle according to an embodiment, in which region A surrounded with a dashed line in FIG. 1 is shown in a magnified manner in FIG. 2A, $CH_3$—$(CH_2)_5$— is shown as an example of the alkyl group included in the covering layer 3. This alkyl group is bonded to the cladding 2 via a bond. In FIG. 2A, there exists an alkyl group bonded to a crack (microcrack) 5 on the outer periphery of the cladding 2. Like this alkyl group, an alkyl group may be bonded to the cladding 2 via two or more —Si—O— bonds sharing a Si atom. Alternatively, the Si atom may have a hydroxyl group that is not bonded to the cladding 2. The hydroxyl group may be condensed by dehydration with a hydroxyl group of an adjacent Si atom or with a hydroxyl group existing on the surface of the cladding 2 to produce another —Si—C— bond. The alkyl group is not fluorine-substituted.

It is known that durability and abrasion resistance of a fiber including a core and a cladding are improved by covering the outer periphery of the cladding with a covering layer including an alkyl group which has 8 or more carbon atoms and which is bonded to the cladding via a siloxane bond (Japanese Patent No. 5855798). This technique may not provide sufficient strength to the end of an optical fiber bundle having an end face formed without using a ferrule at the end. However, this problem is solved by limiting the number of carbon atoms of the above alkyl group to 7 or less and thereby improving the adhesive strength. This mechanism will be explained below by comparing FIGS. 2A and 2B.

Figure 2B:
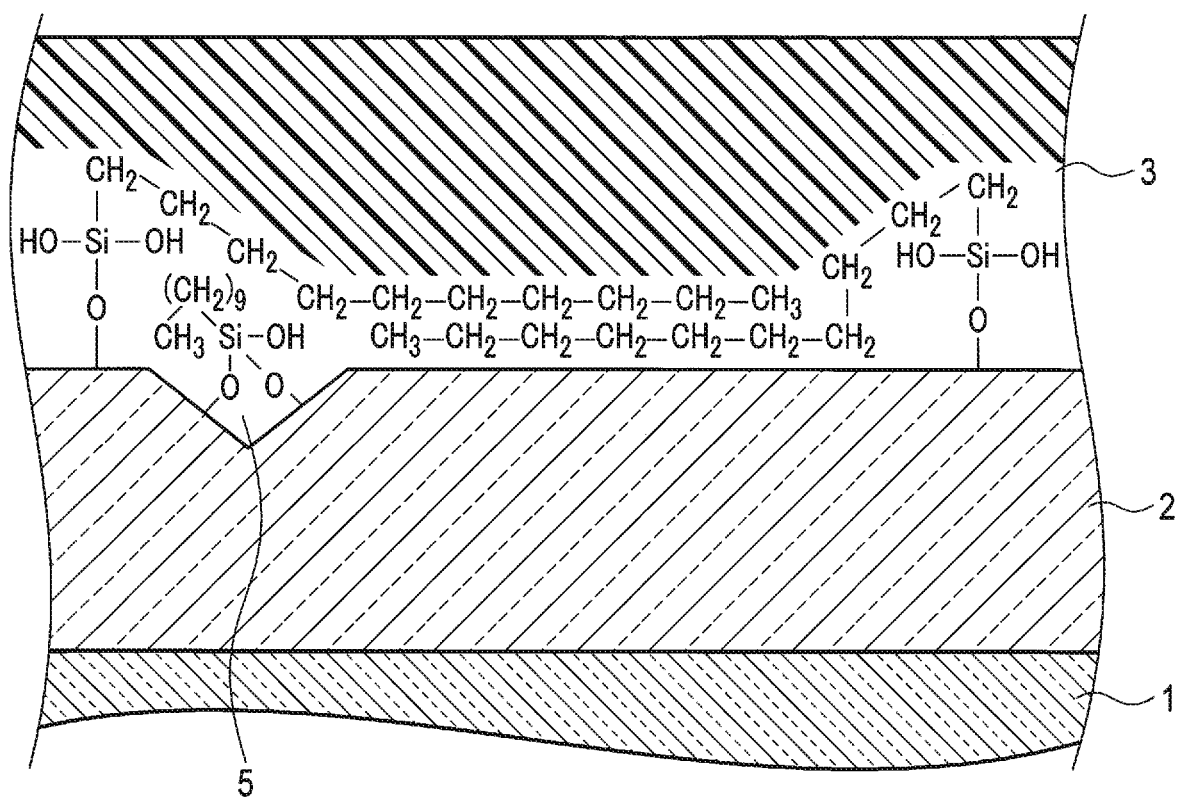
FIG. 2B is a comparative cross-sectional view of the same portion as that shown in FIG. 2A, in which the number of carbon atoms of an alkyl group contained in a covering layer 3 is ten.

FIG. 2B is a comparative cross-sectional view of the same portion as that shown in FIG. 2A, in which the alkyl group contained in the covering layer 103 is represented by $CH_3(CH_2)_9$—, which is an alkyl group having ten carbon atoms. In this case, the durability and abrasion resistance are improved because of the long carbon chain of the alkyl group lying, while the adhesion is lowered because of the carbon chain covering the entire surface of the cladding 102. In FIG. 2A, on the other hand, the alkyl group contained in the covering layer 3 is represented by $CH_3(CH_2)_5$—, which is an alkyl group having six carbon atoms. In this case, the durability and abrasion resistance are improved because of the long carbon chain of the alkyl group lying, and good adhesion is maintained because of the carbon chain not entirely covering the surface of the cladding 2. Therefore, in terms of durability and abrasion resistance, the number of carbon atoms included in the alkyl group is preferably 6 or 7, and m in the formula represented by $CH_3(CH_2)_m$— is preferably 5 or 6.

The covering layer 3 may be formed by applying a treatment liquid that contains alkylsilane including an alkyl group having 1 to 7 carbon atoms and not being fluorine-substituted (hereinafter also referred to as an "alkylsilane treatment liquid"), to the outer periphery of the cladding 2. The method for applying the treatment liquid is not particularly limited. For example, the treatment liquid can be applied by a die coat method, a spray method, a dipping method, or a shower method. The die coat method refers to a method of passing a fiber through a die while supplying a coating liquid to the die to form a covering layer on the surface of the fiber. The spray method refers to a method of spraying a coating liquid on the surface of a fiber. The dipping method refers to a method of immersing a fiber into a coating liquid. The shower method refers to a method of passing a fiber through a shower of a coating liquid.

An example of the alkylsilane included in the treatment liquid is represented by the chemical formula $CH_3(CH_2)_m Si(OR)_n(R')_{3-n}$. In the chemical formula, m is an integer of 0 to 6, and m is preferably 5 or 6. n is an integer of 0 to 3. R is a methyl group (—CH3) or an ethyl group (—CH2CH3). When n is 2 or 3, a plurality of Rs are independent of each other. R' is a hydrogen atom (—H), a methyl group (—$CH_3$), or an ethyl group (—$CH_2CH_3$). When n is 0 or 1, a plurality of R's are independent of each other. An —OR group and an —R' group in the formula change to a hydroxyl group in the treatment liquid, which allows dehydration condensation between the hydroxyl group and a hydroxyl group existing on the surface of the cladding 2.

The treatment liquid may include a dispersant and water in addition to alkylsilane. Examples of the dispersant include an organic solvent, a surfactant, and the like. Examples of the surfactant include a cationic surfactant. Examples of the cationic surfactant include didodecyldimethylammonium chloride, cetyltrimethylammonium chloride, hexadecyltrimethylammonium chloride, tetradecyltrimethylammonium chloride, and the like. Examples of the organic solvent include ethyl alcohol, isopropyl alcohol, and the like.

An optical transmission element included in the optical fiber bundle according to the embodiment is preferably free of lead. That is, the fiber and covering layer constituting the optical transmission element are preferably free of lead.

The optical transmission element included in the optical fiber bundle according to the embodiment may further include a solid lubricant applied to the outer periphery of the covering layer. The presence of the solid lubricant on the outer periphery of the covering layer can inhibit close contact between optical transmission elements upon bundling, and can prevent the optical transmission elements from sticking to each other even if they are subjected to washing, disinfection, and sterilization operations with high temperature/pressure water vapor (autoclave) or a medicinal solution. In addition, the presence of the solid lubricant can impart resistance to breaking of the optical fiber bundle.

Examples of the solid lubricant include talc, boron nitride, molybdenum disulfide, fluoride resins such as ethylene fluoride, polyacetal, carbon graphite, and the like.

Figure 3:
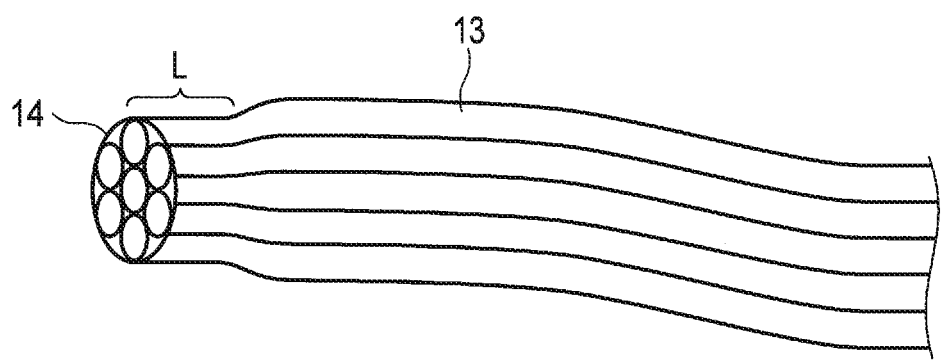
FIG. 3 is a schematic perspective view of an example of the main part of an optical fiber bundle according to an embodiment.

FIG. 3 shows an example of the main part including an end L of an optical fiber bundle according to an embodiment. In this example, bundled optical transmission elements 13 constitute the optical fiber bundle. The end L having a polished end face 14 is fixed with an adhesive without a ferrule covering the outer periphery of the end.

The optical fiber bundle according to the embodiment can be used as, for example, an image guide or a light guide.

The optical fiber bundle of the present invention has high adhesion between optical transmission elements and excellent end strength with its performance such as durability necessary for satisfying the endoscope observation performance maintained. This enables formation of the end into a desired shape without using a ferrule, which in turn enables provision of an endoscope that meets the demand for a smaller diameter.

A second embodiment of the present invention relates to an endoscope. The endoscope includes at least one of the image guide according to the embodiment and the light guide according to the embodiment.

Figure 4:
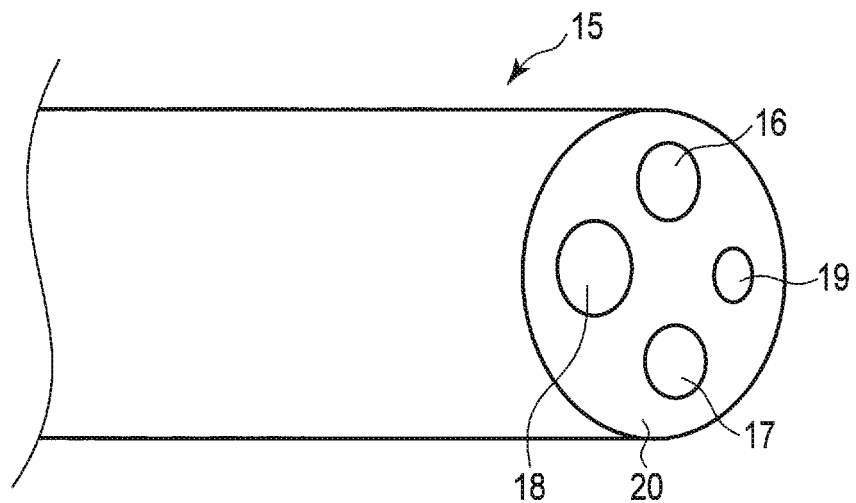
FIG. 4 is a diagram showing an example of a tip part of an endoscope according to an embodiment.

FIG. 4 shows an example of a tip part of an endoscope according to an embodiment. In an endoscope 15 in this example, an image guide 16 and a light guide 17 are inserted into a tip element 20. The tip element 20 is provided with a forceps port 18 used for inserting and removing a treatment instrument for collecting a tissue or excising a lesion, as well as a nozzle 19 for sending out water for cleaning a lens or air for swelling a body cavity.

A third embodiment of the present invention relates to a method of producing an optical fiber bundle.

The optical fiber bundle according to the embodiment is fixed at least at one end with an adhesive, and is free from a ferrule covering an outer periphery of the end in one embodiment, as described above. Such an optical fiber bundle can be produced by, for example, the method to be described below.

First, an optical transmission element according to the embodiment is obtained by applying the above-described alkylsilane treatment liquid to the outer periphery of a fiber including a core and a cladding using the above-described method, to form a covering layer.

Figure 5:
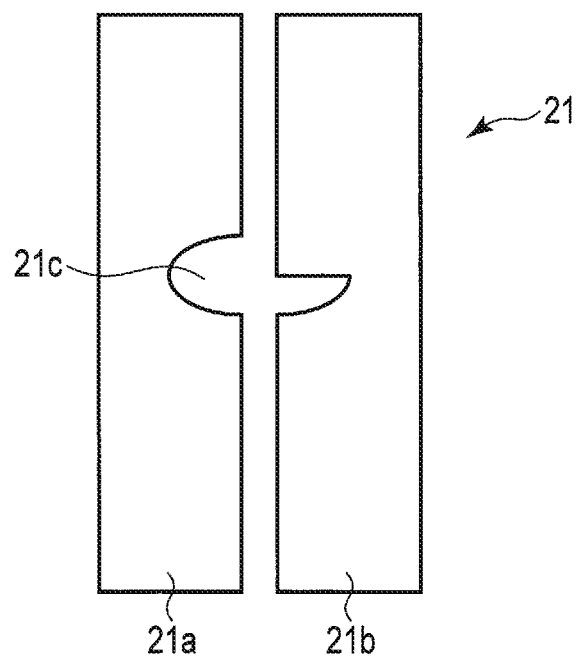
FIG. 5 is a front view of an example of a jig used in producing an optical fiber bundle according to an embodiment.

Next, a plurality of the optical transmission elements are bundled, and at least one end of the obtained bundle of optical transmission elements is fixed without using a ferrule. As means for fixing the end of the bundle of optical transmission elements, for example, an adhesive and a jig having a through hole into which an end of the bundle is inserted and by which the end is formed into a predetermined shape are used. FIG. 5 shows an example of the jig. In FIG. 5, a jig 21 includes left and right half-split attachment components 21a and 21b. The jig is provided with a through hole 21c at its center, into which the end of the bundle of optical transmission elements is to be inserted.

In the fixing means using the jig 21, at least one end of the bundle of optical transmission elements is inserted into the through hole 21c of the jig 21 until the tip part of the bundle protrudes. The length of the tip part of the bundle protruding from the through hole 21c is appropriately set.

An adhesive is then applied to the end of the bundle including a protrusion that protrudes from the through hole 21c so as to fix the end.

Subsequently, the fixed end is subjected to cutting of the protrusion and polishing of the end face, followed by removing the jig 21. The fixed end has a shape identical with that of the through hole 21c of the jig 21.

The optical fiber bundle according to the embodiments has a higher strength at its fixed end than a conventional optical fiber bundle because optical transmission elements are each firmly fixed due to a strong adhesion between the optical transmission elements. For this reason, the end is not damaged at the time of cutting the protrusion, polishing the end face, or releasing the jig. Therefore, the optical fiber bundle is suitable for use in an image guide or light guide that has no ferrule covering the outer periphery of the end, and thus can be used favorably for an endoscope required to have a smaller diameter.

The optical fiber bundle according to the embodiments can achieve excellent advantageous effects in addition to those described above.

Figure 6:
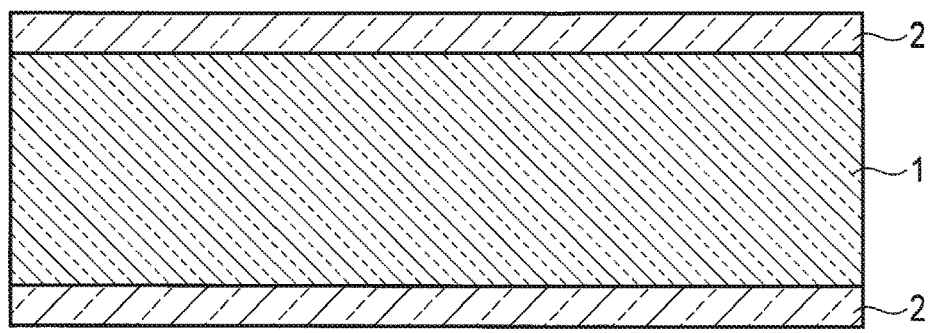
FIG. 6 is an axial cross-sectional view of a conventional optical transmission element that is not covered.
Figure 7:
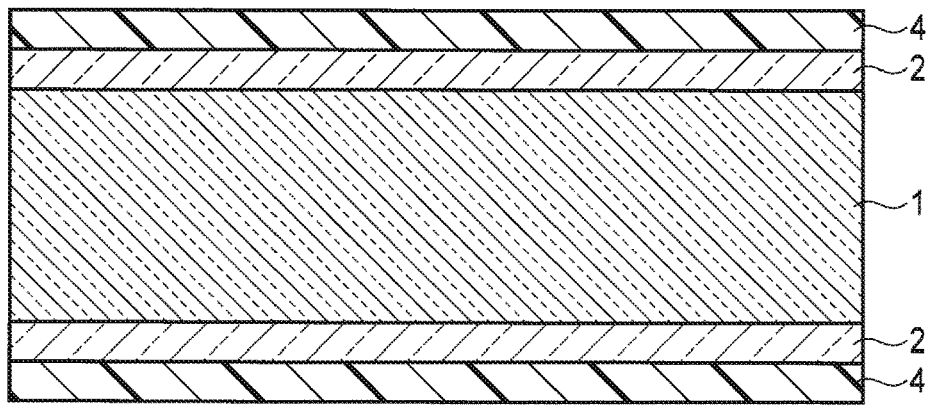
FIG. 7 is an axial cross-sectional view of a conventional optical transmission element that is covered with a fluorinated alkylsilane layer.
Figure 8:
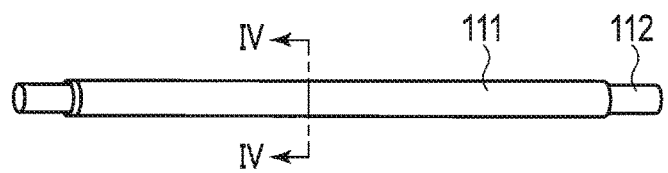
FIG. 8 is a schematic perspective view of a light guide or image guide having ferrules.
Figure 9:
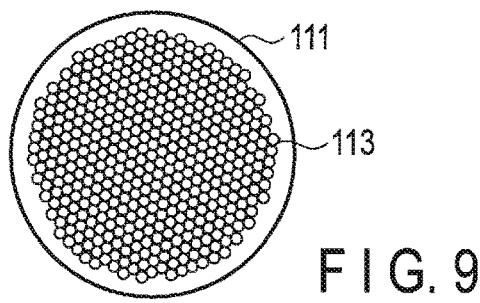
FIG. 9 is a cross-sectional view of the image guide or light guide taken along line IV-IV in FIG. 8.

FIGS. 6 and 7 show examples of a conventional optical transmission element. FIG. 6 is an axial cross-sectional view of a conventional optical transmission element that is not covered. FIG. 7 is an axial cross-sectional view of a conventional optical transmission element that is covered with a fluorinated alkylsilane layer 4.

An optical transmission element having no covering layer as shown in FIG. 6 has poorer durability, abrasion resistance, and lubricity than an optical transmission element having a covering layer. In particular, a fiber made of lead-free glass is harder and less flexible in terms of physical properties than a lead-containing fiber. Therefore, a fiber of an image guide or light guide including bundled optical transmission elements which are made of lead-free glass and which have no covering layer is frequently broken when the image guide or light guide is repeatedly severely bent in the tip part of the endoscope, which leads to deterioration in observation performance of the endoscope.

An optical transmission element having a fluorinated alkylsilane layer 4 as shown in FIG. 7 has excellent durability, abrasion resistance, and lubricity due to the presence of the fluorinated alkylsilane layer, which can reduce the breaking and deterioration to such an extent that sufficient observation performance is obtained. However, the fluorinated alkyl group in the fluorinated alkylsilane layer exposed at the surface of the optical transmission element decreases the adhesion between a plurality of the optical transmission elements when the optical transmission elements are bundled.

In general, when an image guide or light guide used for an endoscope is produced, a plurality of optical transmission elements are bundled and stored in a jacket tube, and then end faces are polished. This improves optical transparency due to polishing of the end faces of each optical transmission element, and achieves alignment of the end faces of the plurality of optical transmission elements. However, when the adhesion between the optical transmission elements is low as in the case where the optical transmission element having the fluorinated alkylsilane layer 4 is used, the fixation of each optical transmission element is insufficient, which makes the polishing difficult. In this case, the edge of the end face of each optical transmission element is scraped, or the optical transmission elements are partly buried. As a result, there is a problem that the observation performance of the endoscope is deteriorated.

EXAMPLES

An optical fiber bundle according to an embodiment was produced, and the durability and adhesion of the bundle were evaluated.
<Preparation of Alkylsilane Treatment Liquid>
As the alkylsilane (general formula $CH_3(CH_2)_m Si(OR)_n (R')_{3-n}$) and a dispersant, compounds listed in Table 1 provided below were used.

By mass, 0.01 to 20% of alkylsilane and 0 to 20% of a dispersant were dissolved in water to prepare 12 alkylsilane treatment liquids (i) to (xii) shown in Table 1 (Examples 1 to 6, Comparative Examples 1 to 6). The total amount of alkylsilane and dispersant was set to 30% by mass or less.

For a comparative example, 0.01 to 10% by mass of a fluorine-substituted alkyl group-containing organic silicon compound in place of alkylsilane represented by the general formula $CH_3(CH_2)_m Si(OR)_n (R')_{3-n}$, was dissolved in a fluorine-based solvent to prepare a treatment liquid (xiii)

Comparative Example 7

<Application of Treatment Liquid to Fiber>
A fiber was immersed into each of the 8 treatment liquids prepared as described above for 10 seconds. An optical transmission element including a fiber and a covering layer was thereby obtained.
<Production of Optical Fiber Bundle>
A plurality of the optical transmission elements produced above were bundled to obtain a bundle of optical transmission elements. One end of the bundle of optical transmission elements was inserted into a through hole of a jig composed of a half-split attachment until a tip part of the end protruded.

An adhesive was then applied to the end of the bundle including a protrusion that protrudes from the through hole to fix the end. Subsequently, the protrusion was cut and the end face was polished, followed by removing the bundle from the half-split attachment, which is the jig. In this way, 13 types of optical fiber bundles were obtained.

Durability and adhesion were evaluated for each of the 13 types of bundles by the method described below.
<Evaluation of Durability>
For the evaluation, a test was carried out by simulating a load applied to an end of a bundle of optical transmission elements when an insertion portion of an endoscope was repeatedly bent. Specifically, for each of the 13 types of bundles, after a higher load than that in the case of manipulating the endoscope was repeatedly applied to the vicinity of the center in the longitudinal direction of the bundle a given number of times, the number of the broken optical transmission elements was counted. From the result, a breaking rate (%) was calculated according to the following formula:

breaking rate (%)=(number of optical transmission elements broken after test)/(total number of optical transmission elements)×100

The results were summarized in Table 1 below. In Table 1, a bundle having a breaking rate of less than 20% was evaluated as "A". A bundle having a breaking rate of 20% or more and less than 70% was evaluated as "B". A bundle having a breaking rate of 70% or more and less than 75% was evaluated as "C". A bundle having a breaking rate of 75% or more was evaluated as "D".

Of the evaluations A to D, C is a level that satisfies the durability required for observation performance of an endoscope.
<Evaluation of Adhesion>
An adhesion at the end of the bundle was evaluated by the following method.

For each of the examples and comparative examples, three bundles of optical transmission elements before end molding were prepared. The ends of their respective bundles were molded using the following three types of jigs a, b, and c, which have different through-hole shapes. The adhesion of the end of the bundle was evaluated based on whether the end was cracked when the end of the bundle was removed from each jig (half-split attachment). The evaluation criteria are as follows.
[Jig]
Jig a: The shape of the through hole is a non-circular shape having a corner in part.
Jig b: The shape of the through hole is a non-circular shape having no corners.
Jig c: The shape of the through hole is a circular shape.
[Evaluation Criteria]
A: No crack occurred and end molding was achieved when either of jig a, jig b, and jig c was used.
B: A crack occurred at the end when jig a was used, but no crack occurred and end molding was achieved when jig b or jig c was used.
C: A crack occurred at the end when jig a or b was used, but no crack occurred and end molding was achieved when jig c was used.
D: A crack occurred when either of jig a, jig b, and jig c was used.

TABLE 1

| Treatment Liquid | | Component name | Substance name | Durability | Adhesion |
|---|---|---|---|---|---|
| Example 1 | (i) | Active ingredient | Methyltrimethoxysilane (m = 0, n = 3, R = CH3) | C | A |
| | | Dispersant | — | | |
| | | Solvent | Water | | |
| Example 2 | (ii) | Active ingredient | Methyltriethoxysilane (m = 0, n = 3, R = CH2CH3) | C | A |
| | | Dispersant | — | | |
| | | Solvent | Water | | |
| Example 3 | (iii) | Active ingredient | Hexyltrimethoxysilane (m = 5, n = 3, R = CH3) | B | A |
| | | Dispersant | Didodecyldimethylammonium Chloride | | |
| | | Solvent | Water | | |
| Example 4 | (iv) | Active ingredient | Hexyltrimetlaoxysilane (m = 5, n = 3, R = CH3) | B | A |
| | | Dispersant | Cetyltrimethylammonium Chloride | | |
| | | Solvent | Water | | |
| Example 5 | (v) | Active ingredient | Hexyltriethoxysilane (m = 5, n = 3, R = CH2CH3) | B | A |
| | | Dispersant | Didodecyldimethylammonium Chloride | | |
| | | Solvent | Water | | |
| Example 6 | (vi) | Active ingredient | Hexyltriethoxysilane (m = 5, n = 3, R = CH2CH3) | B | A |
| | | Dispersant | Cetyltrimethylammonium Chloride | | |
| | | Solvent | Water | | |
| Comparative Example 1 | (vii) | Active ingredient | n-Octyltrimethoxysilane (m = 7, n = 3, R = CH3) | A | B |
| | | Dispersant | Didodecyldimethylammonium Chloride | | |
| | | Solvent | Water | | |
| Comparative Example 2 | (viii) | Active ingredient | n-Octyltrimethoxysilane (m = 7, n = 3, R = CH3) | A | B |
| | | Dispersant | Cetyltrimethylammonium Chloride | | |
| | | Solvent | Water | | |
| Comparative Example 3 | (ix) | Active ingredient | n-Octyltriethoxysilane (m = 7, n = 3, R = CH2CH3) | A | B |
| | | Dispersant | Didodecyldimethylammonium Chloride | | |
| | | Solvent | Water | | |
| Comparative Example 4 | (x) | Active ingredient | n-Octyltriethoxysilane (m = 7, n = 3, R = CH2CH3) | A | B |
| | | Dispersant | Cetyltrimethylammonium Chloride | | |
| | | Solvent | Water | | |
| Comparative Example 5 | (xi) | Active ingredient | Decyltrimethoxysilane (m = 9, n = 3, R = CH3) | A | C |
| | | Dispersant | Didodecyldimethylammonium Chloride | | |
| | | Solvent | Water | | |
| Comparative Example 6 | (xii) | Active ingredient | Decyltrimethoxysilane (m = 9, n = 3, R = CH3) | A | C |
| | | Dispersant | Cetyltrimethylammonium Chloride | | |
| | | Solvent | Water | | |
| Comparative Example 7 | (xiii) | Active ingredient | Fluorine-substituted alkyl group-containing organic silicon compound | A | D |
| | | Dispersant | — | | |
| | | Solvent | Fluorine-based solvent | | |

From the results shown in Table 1, the following is found. Examples 1 to 6, in which the alkyl group of the alkylsilane has 7 or less carbon atoms (m is 6 or less), exhibit extremely excellent adhesive strength of the end as well as durability required for the observation performance of an endoscope, which enables special molding without using a ferrule, and can be favorably used for an endoscope required to have a smaller diameter.

The present invention is not limited to the above-described embodiments, and can be variously modified in practice, without departing from the gist of the invention. In addition, the embodiments may be suitably combined for implementation, to obtain combined effects. Furthermore, the above embodiments include various inventions, and various inventions can be extracted by an appropriate combination of the constituent elements disclosed herein. For example, even if several constituent elements are removed from all the constituent elements shown in an embodiment, the configuration from which the constituent elements are removed can be extracted as an invention as long as the configuration solves the problem and delivers an advantageous effect.

What is claimed is:

1. An optical fiber bundle comprising:
a bundle of optical transmission elements, each optical transmission element including:
a fiber including a core made of a first glass and a cladding made of a second glass and covering an outer periphery of the core; and
a covering layer covering an outer periphery of the cladding,
wherein the optical fiber bundle is fixed at at least one end with an adhesive, and is free from a ferrule covering an outer periphery of the fixed end, and
wherein the covering layer includes an alkyl group having 1 to 7 carbon atoms and not being fluorine-substituted, and the alkyl group is bonded to the cladding via a siloxane bond.

2. The optical fiber bundle according to claim 1, wherein the alkyl group has 6 or 7 carbon atoms.

3. The optical fiber bundle according to claim 1, wherein the alkyl group is represented by $CH_3(CH_2)_m$—, where m represents an integer of 0 to 6.

4. The optical fiber bundle according to claim 3, wherein m in the formula representing the alkyl group is 5 or 6.

5. The optical fiber bundle according to claim 1, wherein the covering layer further includes a surfactant.

6. The optical fiber bundle according to claim 1, wherein the optical fiber bundle is an image guide.

7. The optical fiber bundle according to claim 1, wherein the optical fiber bundle is a light guide.

8. An endoscope comprising the optical fiber bundle according to claim 1.

9. A method of producing the optical fiber bundle according to claim 1, comprising:
applying a treatment liquid including alkylsilane which includes an alkyl group having 1 to 7 carbon atoms and not being fluorine-substituted, to the outer periphery of the cladding covering the outer periphery of the core, to form the covering layer on the outer periphery of the cladding, thereby obtaining each of the optical transmission elements;

bundling a plurality of the optical transmission elements to obtain a bundle of optical transmission elements;

preparing a jig including a through hole into which an end of the bundle is to be inserted;

inserting at least one end of the bundle into the through hole of the jig until a tip part of the end protrudes;

applying an adhesive to the end of the bundle including a protrusion that protrudes from the through hole to fix the end; and cutting the protrusion and polishing an end face.

10. The method of producing the optical fiber bundle according to claim 9, wherein the alkyl group has 6 or 7 carbon atoms.

11. The method of producing the optical fiber bundle according to claim 9, wherein the alkylsilane is represented by $CH_3(CH_2)_m Si(OR)_n(R')_{3-n}$ where m represents an integer of 0 to 6, n represents an integer of 0 to 3, each R independently represents a methyl group or an ethyl group, and each R' independently represents a hydrogen atom, a methyl group, or an ethyl group.

12. The method of producing the optical fiber bundle according to claim 11, wherein m in the formula representing the alkylsilane is 5 or 6.

13. The method of producing the optical fiber bundle according to claim 9, wherein the optical fiber bundle is an image guide.

14. The method of producing the optical fiber bundle according to claim 9, wherein the optical fiber bundle is a light guide.

15. The method of producing the optical fiber bundle according to claim 9, wherein the treatment liquid further includes a surfactant.

* * * * *